(12) United States Patent
Gentalen et al.

(10) Patent No.: US 8,945,361 B2
(45) Date of Patent: Feb. 3, 2015

(54) ELECTROPHORESIS STANDARDS, METHODS AND KITS

(75) Inventors: Erik Gentalen, Mountain View, CA (US); Daniel J. Suich, Oakland, CA (US)

(73) Assignee: ProteinSimple, Santa Clara, CA (US)

( * ) Notice: Subject to any disclaimer, the term of this patent is extended or adjusted under 35 U.S.C. 154(b) by 1915 days.

(21) Appl. No.: 11/524,630

(22) Filed: Sep. 20, 2006

(65) Prior Publication Data

US 2007/0062813 A1 Mar. 22, 2007

Related U.S. Application Data

(60) Provisional application No. 60/719,246, filed on Sep. 20, 2005.

(51) Int. Cl.
| | |
|---|---|
| G01N 27/447 | (2006.01) |
| C07K 1/13 | (2006.01) |
| C07K 1/26 | (2006.01) |
| C07K 1/28 | (2006.01) |
| C07K 7/06 | (2006.01) |
| C07K 7/08 | (2006.01) |

(52) U.S. Cl.
CPC ............ *G01N 27/44726* (2013.01); *C07K 1/13* (2013.01); *C07K 1/26* (2013.01); *C07K 1/28* (2013.01); *C07K 7/06* (2013.01); *C07K 7/08* (2013.01); *G01N 2550/00* (2013.01)
USPC ............................. 204/548; 204/450; 204/644

(58) Field of Classification Search
USPC .................. 204/451–455, 548, 601–605, 644
See application file for complete search history.

(56) References Cited

U.S. PATENT DOCUMENTS

| | | |
|---|---|---|
| 1,015,891 A | 1/1912 | Ikeda et al. |
| 2,509,399 A | 5/1950 | Resek |
| 3,669,955 A | 6/1972 | Hull |
| 4,021,364 A | 5/1977 | Speiser et al. |
| 4,128,470 A | 12/1978 | Hiratsuka et al. |
| 4,666,855 A | 5/1987 | Yang et al. |
| 4,680,201 A | 7/1987 | Hjerten |
| 4,716,101 A | 12/1987 | Thompson et al. |
| 4,788,138 A | 11/1988 | Tung et al. |

(Continued)

FOREIGN PATENT DOCUMENTS

| | | |
|---|---|---|
| CA | 2559870 | 10/2005 |
| CA | 2806640 | 2/2012 |

(Continued)

OTHER PUBLICATIONS

Determination of Isoelectric Point and Investigation of Immunoreaction in Peanut Allergenic Proteins-Rabbit IgG Antibody System by Whole-Column Imaged Capillary Isoelectric Focusing, J. Microcolumn Separation, 13(8) 322-326, 2001.*

(Continued)

*Primary Examiner* — Luan Van
*Assistant Examiner* — Gurpreet Kaur

(57) ABSTRACT

Electrophoresis Compositions, methods and kits useful for, among other things, detecting, quantifying and/or characterizing analytes are provided. The compositions are useful as electrophoresis standards for determine the isoelectric point and molecular weight of an analyte. The electrophoresis standards generally comprise at least one label moiety and one or more reactive moieties that when activated attach the standard to a substrate.

8 Claims, 5 Drawing Sheets

(56) References Cited

U.S. PATENT DOCUMENTS

| | | | |
|---|---|---|---|
| 4,810,781 A | 3/1989 | Hollinshead | |
| 4,843,010 A | 6/1989 | Nowinski et al. | |
| 4,870,003 A | 9/1989 | Kortright et al. | |
| 4,921,790 A | 5/1990 | O'Brien | |
| 5,002,582 A | 3/1991 | Guire et al. | |
| 5,074,982 A | 12/1991 | Novotny et al. | |
| 5,096,807 A | 3/1992 | Leaback | |
| 5,106,951 A | 4/1992 | Morgan, Jr. et al. | |
| 5,110,434 A | 5/1992 | Zhu et al. | |
| 5,137,609 A | 8/1992 | Manian et al. | |
| 5,143,753 A | 9/1992 | Novotny et al. | |
| 5,180,475 A | 1/1993 | Young et al. | |
| 5,228,960 A | 7/1993 | Liu et al. | |
| 5,244,813 A | 9/1993 | Walt et al. | |
| 5,260,028 A | 11/1993 | Astle | |
| 5,264,101 A | 11/1993 | Demorest et al. | |
| 5,266,273 A | 11/1993 | Coombs | |
| 5,290,418 A | 3/1994 | Menchen et al. | |
| 5,348,633 A | 9/1994 | Karger et al. | |
| 5,370,777 A | 12/1994 | Guttman et al. | |
| 5,376,249 A | 12/1994 | Afeyan et al. | 204/452 |
| 5,395,502 A | 3/1995 | Pawliszyn | |
| 5,417,922 A | 5/1995 | Markin et al. | |
| 5,468,359 A | 11/1995 | Pawliszyn | |
| 5,468,365 A | 11/1995 | Menchen et al. | |
| 5,479,969 A | 1/1996 | Hardie et al. | |
| 5,482,867 A | 1/1996 | Barrett et al. | |
| 5,552,028 A | 9/1996 | Madabhushi et al. | |
| 5,567,292 A | 10/1996 | Madabhushi et al. | |
| 5,614,073 A | 3/1997 | Bobbitt et al. | |
| 5,622,871 A | 4/1997 | May et al. | |
| 5,627,643 A | 5/1997 | Birnbaum et al. | |
| 5,630,924 A | 5/1997 | Fuchs et al. | |
| 5,633,129 A | 5/1997 | Karger et al. | |
| 5,759,369 A | 6/1998 | Menchen et al. | |
| 5,759,770 A | 6/1998 | Guertler et al. | |
| 5,784,154 A | 7/1998 | Pawliszyn | |
| 5,785,926 A | 7/1998 | Seubert et al. | |
| 5,798,035 A | 8/1998 | Kirk et al. | |
| 5,804,384 A | 9/1998 | Muller et al. | |
| 5,822,055 A | 10/1998 | Tsai et al. | |
| 5,830,539 A | 11/1998 | Yan et al. | 427/551 |
| 5,835,211 A | 11/1998 | Wells et al. | |
| 5,840,388 A | 11/1998 | Karger et al. | |
| 5,840,503 A | 11/1998 | Beausang et al. | |
| 5,843,680 A | 12/1998 | Manian et al. | |
| 5,853,744 A * | 12/1998 | Mooradian et al. | 424/422 |
| 5,858,188 A | 1/1999 | Soane et al. | |
| 5,866,683 A * | 2/1999 | Shimura et al. | 530/328 |
| 5,882,864 A | 3/1999 | An et al. | |
| 5,932,080 A | 8/1999 | Likuski | |
| 5,935,401 A | 8/1999 | Amigo | |
| 5,963,456 A | 10/1999 | Klein et al. | |
| 5,976,336 A | 11/1999 | Dubrow et al. | |
| 5,976,896 A | 11/1999 | Kumar et al. | |
| 5,985,121 A | 11/1999 | Wu et al. | |
| 6,054,032 A | 4/2000 | Haddad et al. | 204/451 |
| 6,056,860 A | 5/2000 | Amigo | |
| 6,061,130 A | 5/2000 | Plate et al. | |
| 6,074,542 A | 6/2000 | Dolnick et al. | |
| 6,087,188 A | 7/2000 | Johansen et al. | |
| 6,100,045 A | 8/2000 | Van Es | |
| 6,107,038 A | 8/2000 | Choudhary et al. | |
| 6,111,238 A | 8/2000 | Fix et al. | |
| 6,126,870 A | 10/2000 | Akhavan-Tafti | |
| 6,139,797 A | 10/2000 | Suzuki et al. | |
| 6,165,800 A | 12/2000 | Jiang et al. | |
| 6,197,173 B1 | 3/2001 | Kirkpatrick | 204/478 |
| 6,208,941 B1 | 3/2001 | Marks | |
| 6,254,634 B1 | 7/2001 | Anderson et al. | |
| 6,280,960 B1 | 8/2001 | Carr | |
| 6,287,767 B1 | 9/2001 | Bronstein et al. | |
| 6,322,970 B1 * | 11/2001 | Little et al. | 506/6 |
| 6,326,083 B1 | 12/2001 | Yang et al. | |
| 6,348,596 B1 | 2/2002 | Lee et al. | |
| 6,355,709 B1 | 3/2002 | Madabhushi et al. | |
| 6,358,385 B1 | 3/2002 | Madabhushi et al. | |
| 6,375,817 B1 | 4/2002 | Taylor et al. | |
| 6,387,236 B2 | 5/2002 | Nordman et al. | |
| 6,395,503 B1 | 5/2002 | Suzuki et al. | |
| 6,423,536 B1 | 7/2002 | Jovanovich et al. | |
| 6,430,512 B1 | 8/2002 | Gallagher | |
| 6,461,492 B1 | 10/2002 | Hayashizaki et al. | |
| 6,475,364 B1 | 11/2002 | Dubrow et al. | |
| 6,522,781 B1 | 2/2003 | Norikane et al. | |
| 6,589,789 B1 | 7/2003 | Hubert et al. | |
| 6,689,576 B2 | 2/2004 | Matsuno et al. | |
| 6,787,016 B2 | 9/2004 | Tan et al. | |
| 6,794,671 B2 | 9/2004 | Nicoli et al. | |
| 6,818,112 B2 | 11/2004 | Schneider et al. | |
| 6,835,715 B1 | 12/2004 | Valdes et al. | |
| 6,849,396 B2 | 2/2005 | Schneider | |
| 6,852,206 B2 | 2/2005 | Pawliszyn et al. | |
| 6,878,256 B2 | 4/2005 | Kasai et al. | |
| 6,878,340 B2 | 4/2005 | Heath et al. | |
| 6,919,044 B1 | 7/2005 | Shibata et al. | |
| 7,018,587 B2 | 3/2006 | Heath et al. | |
| 7,064,826 B2 | 6/2006 | Rabinski et al. | |
| 7,217,937 B2 | 5/2007 | King | |
| 7,300,523 B2 | 11/2007 | Lee et al. | |
| 7,307,721 B2 | 12/2007 | King | |
| 7,309,593 B2 | 12/2007 | Ofstead et al. | |
| 7,316,770 B2 | 1/2008 | Inaba et al. | |
| 7,340,324 B2 | 3/2008 | Heath et al. | |
| 7,374,724 B2 | 5/2008 | Ingenhoven et al. | |
| 7,379,577 B2 | 5/2008 | King et al. | |
| 7,399,600 B2 | 7/2008 | Carr | |
| 7,471,393 B2 | 12/2008 | Trainer | |
| 7,564,623 B2 | 7/2009 | Vodyanoy et al. | |
| 7,605,919 B2 | 10/2009 | Oma et al. | |
| 7,634,125 B2 | 12/2009 | Ortyn et al. | |
| 7,846,676 B2 | 12/2010 | Yang et al. | |
| 7,935,308 B2 | 5/2011 | O'Neill et al. | |
| 7,935,479 B2 | 5/2011 | O'Neill et al. | |
| 7,935,489 B2 | 5/2011 | O'Neill et al. | |
| 8,000,905 B1 | 8/2011 | Chen et al. | |
| 2002/0029968 A1 | 3/2002 | Tan et al. | |
| 2002/0071847 A1 | 6/2002 | Sadziene et al. | |
| 2002/0110900 A1 | 8/2002 | Jovanovich et al. | |
| 2002/0115740 A1 | 8/2002 | Beuhler et al. | |
| 2002/0123134 A1 | 9/2002 | Huang et al. | |
| 2003/0032035 A1 | 2/2003 | Chatelain et al. | |
| 2003/0078314 A1 | 4/2003 | Johnson et al. | |
| 2003/0128043 A1 | 7/2003 | Zeltz et al. | |
| 2003/0175820 A1 | 9/2003 | Smith et al. | 435/7.2 |
| 2003/0175986 A1 | 9/2003 | Patricelli | 436/172 |
| 2004/0021068 A1 | 2/2004 | Staats | 250/288 |
| 2004/0078219 A1 * | 4/2004 | Kaylor et al. | 705/2 |
| 2004/0166546 A1 | 8/2004 | Warmington et al. | |
| 2004/0168917 A1 | 9/2004 | Tabuchi et al. | |
| 2004/0181443 A1 | 9/2004 | Horton et al. | 705/8 |
| 2004/0224362 A1 | 11/2004 | Gjerde et al. | |
| 2004/0262160 A1 | 12/2004 | Schneider et al. | |
| 2005/0054083 A1 | 3/2005 | Vuong et al. | 435/287.2 |
| 2005/0082170 A1 | 4/2005 | Provost et al. | |
| 2005/0115837 A1 | 6/2005 | Burgi | |
| 2005/0155861 A1 | 7/2005 | Guzman | |
| 2005/0176070 A1 | 8/2005 | Auton | |
| 2005/0242963 A1 | 11/2005 | Oldham et al. | |
| 2005/0249882 A1 | 11/2005 | Liu et al. | |
| 2006/0029978 A1 * | 2/2006 | O'Neill et al. | 435/7.1 |
| 2006/0030669 A1 | 2/2006 | Taton et al. | |
| 2006/0057576 A1 | 3/2006 | Paszkowski et al. | |
| 2006/0254914 A1 | 11/2006 | Biron et al. | |
| 2006/0292558 A1 | 12/2006 | O'Neill | |
| 2006/0292649 A1 | 12/2006 | Cahill et al. | |
| 2008/0009078 A1 | 1/2008 | O'Neill | |
| 2008/0017512 A1 | 1/2008 | Bordunov et al. | |
| 2008/0035484 A1 | 2/2008 | Wu et al. | |
| 2008/0037004 A1 | 2/2008 | Shamir et al. | |
| 2008/0254552 A1 | 10/2008 | O'Neill | |
| 2009/0023156 A1 | 1/2009 | Voss et al. | |
| 2009/0023225 A1 | 1/2009 | Yang | |
| 2009/0194419 A1 | 8/2009 | Huang et al. | |

(56) References Cited

U.S. PATENT DOCUMENTS

| | | |
|---|---|---|
| 2010/0155241 A1 | 6/2010 | Ross et al. |
| 2010/0188499 A1 | 7/2010 | Amanullah et al. |
| 2011/0011740 A1 | 1/2011 | Roach et al. |
| 2011/0132761 A1 | 6/2011 | O'Neill |
| 2011/0195527 A1 | 8/2011 | O'Neill |
| 2012/0068068 A1 | 3/2012 | Hill et al. |
| 2012/0274760 A1 | 11/2012 | King et al. |
| 2013/0167937 A1 | 7/2013 | Roach et al. |
| 2013/0280815 A1 | 10/2013 | Wu |
| 2014/0021053 A1 | 1/2014 | Wu et al. |
| 2014/0106372 A1 | 4/2014 | Yang et al. |

FOREIGN PATENT DOCUMENTS

| | | | |
|---|---|---|---|
| CA | 2775506 | 10/2012 | |
| EP | 0 665 430 A1 | 1/1994 | |
| EP | 0 805 215 A1 | 11/1997 | |
| EP | 1 236 738 A1 | 9/2002 | |
| JP | 05-172815 A | 7/1993 | |
| JP | H08-503775 | 4/1996 | |
| JP | 2007-506432 A | 3/2007 | |
| WO | WO 94/12871 | 6/1994 | |
| WO | WO 94/13829 A1 | 6/1994 | |
| WO | WO 9963408 A1 | 12/1999 | |
| WO | WO 00/42423 A1 | 7/2000 | |
| WO | WO 01/55721 A2 | 8/2001 | |
| WO | WO 02/00746 A2 | 1/2002 | |
| WO | WO 02/14851 * | 2/2002 | ............ G01N 27/00 |
| WO | WO 03/100086 | 12/2003 | |
| WO | WO 2004/011513 A1 | 2/2004 | |
| WO | WO 2005/032701 A2 | 4/2005 | |
| WO | WO 2005/033158 A2 | 4/2005 | |
| WO | WO 2005/084191 | 9/2005 | |
| WO | WO 2006/014680 | 2/2006 | |
| WO | WO 2006/084482 A1 | 8/2006 | |
| WO | WO 2006/110725 | 10/2006 | |

OTHER PUBLICATIONS

Shimura et al., Anal. Chem., 2000, 72, 4747-4757.*
Albarghouthi, M., et al., "Poly-N-hydroxyethylacrylamide as a novel, adsorbed coating for protein separation by capillary electrophoresis," *Electrophoresis* 24:1166-1175 (2003).
Chang, W., et al., "Enhanced resolution achieved with electroosmotic flow control in capillary isoelectric focusing with dynamic coatings," *Am. Biotechnol. Lab.* (Apr. 2005).
Doherty, E., et al., "Critical-factors for high-performance physically adsorbed (dynamic) polymeric wall coatings for capillary electrophoresis of DNA," *Electrophoresis* 23:2766-2776 (2002).
Hu, S., et al., "Capillary sodium dodecyl sulfate-DALT electrophoresis of proteins in a single human cancer cell," *Eletrophoresis* 22:3677-3682 (2001).
International Preliminary Report on Patentability International Application No. PCT/US2005/025653, dated Jan. 23, 2007.
International Search Report in International Application No. PCT/US2005/025653, dated Dec. 22, 2005.
Jin, Y., et al., "Estimation of isoelectric points of human plasma proteins employing capillary isoelectric focusing and peptide isoelectric point marks," *Electrophoresis* 22:3385-3391 (2002).
Shmura, H., et al., "Synthetic oligonucleotides as isoelectric point markers for capillary isoelectric focusing with ultraviolet absorption detection," *Electrophoresis* 21:601-610 (2002).
Vilkner, T., et al., "Micro total analysis systems, recent developments," *Anal. Chem.* 76(12):3373-3386 (2004).
Wang, J., et al., "Capillary electrophoresis immunoassay chemiluminescence detection of zeptomoles of bone morphogenic protein-2 in rat vascular smooth muscle cells," *Anal. Chem.* 76:5393-5398 (2004).
Watts, R., et al., "Peptides as standards for denaturing isoelectric focusing," *Electrophoresis* 16:22-25 (1995).
Written Opinion of the International Searching Authority International Application No. PCT/US2005/025653, dated Dec. 22, 2005.
International Search Report and the Written Opinion of International Searching Authority, or the Declaration, for counterpart or related PCT application Serial No. PCT/US 06/13447, dated Aug. 17, 2007.
International Search Report and the Written Opinion of International Searching Authority, or the Declaration, for counterpart or related PCT application Serial No. PCT/US 06/36808, dated Sep. 18, 2007.
Bossi, A., et al., "Capillary Electrophoresis Coupled to Biosensor Detection," J. Chromatography A, 2000, 892, pp. 143-153.
Burnette, W.N., "Western Blotting": Electrophoretic Transfer of Proteins from Sodium Dodecyl Sulfate-Polyacrylamide Gels to Unmodified Nitrocellulose and Radiographic Detection with Antibody and Radioiodinated Protein A, Analytical Biochemistry 112, 1981, pp. 195-203.
Cruickshank, K., et al. "Simultaneous Multiple Analyte Detection Using Fluorescent Peptides and Capillary Isoelectric Focusing," Journal of Chromatography A 817, 1998, pp. 41-47.
Misiakos et al., "A Multi-Band Capillary Immunosensor," Biosensors & Bioelectronics, 1998, 13, pp. 825-830.
Narang et al., "Multianalyte Detection Using a Capillary-Based Flow Immunosensor," Anal. Biochem., 1998, 225, pp. 13-19.
O'Neill, R. A. et al., "Isoelectric Focusing Technology Quantifies Protein Signaling in 25 Cells," PNAS, Oct. 31, 2006, vol. 103, No. 44(31), pp. 16153-16158.
Renart, J. et al., "Transfer of Proteins from Gels to Diazobenzyloxymethyl-paper and Detection with Antisera: A Method for Studying Antibody Specificity and Antigen Structure," Jul. 1979, Proc. Natl. Acad. Sci., USA, vol. 76, No. 7, pp. 3116-3120.
Righetti, P., et al., "Capillary Isolectric Focusing and Isoelectric Buffers: An Evolving Scenario," J Cap Elec. 004, vol. 4, Issue 2, Mar./Apr. 1997, pp. 47-59.
Shimura, K., et al., "Fluorescence-Labeled Peptide p/ Markers for Capillary Isoelectric Focusing," Anal. Chem. 2002, vol. 74, pp. 1046-1053.
Wehr, T., "Capillary Isoelectric Focusing," Methods in Enzymology, vol. 270, pp. 353-374.
International Search Report and Written Opinion for International Application No. PCT/US2005/025653, dated Dec. 12, 2005.
Office Action for U.S. Appl. No. 11/185,247, mailed Jun. 11, 2008.
Office Action for U.S. Appl. No. 11/825,247, mailed Apr. 30, 2009.
Final Office Action for U.S. Appl. No. 11/185,247, mailed Feb. 26, 2010.
Office Action for U.S. Appl. No. 11/431,343, mailed Feb. 3, 2009.
Non-Final Office Action for U.S. Appl. No. 11/431,272, mailed Mar. 20, 2009.
Non-Final Office Action for U.S. Appl. No. 11/725,769, mailed Mar. 3, 2010.
Non-Final Office Action for U.S. Appl. No. 11/981,404, mailed Nov. 16, 2009.
International Search Report and Written Opinion for International Application No. PCT/US2008/081637, dated Jul. 9, 2009.
Annex to form PCT/ISA/206 Communication Relating to the Results of the Partial International Search for PCT/US2008/081637, dated Mar. 16, 2009.
Non-Final Office Action for U.S. Appl. No. 11/981,405, mailed Nov. 13, 2009.
Office Action for U.S. Appl. No. 11/981,405, mailed Jul. 28, 2010.
International Search Report and Written Opinion for International Application No. PCT/US2007/016626, dated Apr. 28, 2008.
Non-Final Office Action for U.S. Appl. No. 11/654,143, mailed Sep. 14, 2010, 16 pages.
Hjerten, S., "High-Performance Electrophoresis Elimination of Electroendosmosis and Solute Adsorption," Journal of Chromatographhy, Elsevier Science Publishers B.V., NL LNKD-doi:10.1016/S0021-9673(01) 95485-8, vol. 347, Nov. 1, 1985, pp. 191-198, XP000575208ISSN: 0021-9673.
Office Action for Japanese Application No. 2007-522674, mailed Mar. 2, 2011.
Office Action for Japanese Application No. 2007-522674, mailed Apr. 11, 2012.
Office Action for Japanese Application No. 2011-148034, mailed Apr. 11, 2012.
Supplemental Search Report for European Application No. 07836214.2, mailed Jun. 21, 2010.

(56) References Cited

OTHER PUBLICATIONS

Office Action for European Application No. 07836214.2, dated Sep. 2, 2011.
Office Action for Japanese Application No. 2009-521800, mailed Jan. 5, 2012.
Non-Final Office Action for U.S. Appl. No. 11/185,247, mailed Oct. 4, 2010.
Final Office Action for U.S. Appl. No. 11/725,769, mailed Oct. 5, 2010.
Office Action for U.S. Appl. No. 13/092,595, mailed Sep. 28, 2012.
Final Office Action for U.S. Appl. No. 11/654,143, mailed May 17, 2011.
Office Action for U.S. Appl. No. 11/975,105, mailed May 10, 2010.
Final Office Action for U.S. Appl. No. 11/975,105, mailed Oct. 19, 2010.
Office Action for U.S. Appl. No. 12/762,830, mailed Jun. 6, 2012.
Archer, D. B. et al., "Hen egg white lysozyme expressed in, and secreted from, *Aspergillus niger* is correctly processed and folded," Biotechnology, 8(8):741-745 (1990).
Bradford, M. M. et al., "A rapid and sensitive method for the quantitation of microgram quantities of protein utilizing the principle of protein-dye binding," Analytical Biochemistry, 72:248-254 (1976).
Breau, A. et al., "Evaluating the bioequivalence of antibody-drug conjugates," Pharmaceutical Technology, Analytical Technology & Testing, pp. s22-s27 (2011).
Canfield, R. E., "The amino acid sequence of egg white lysozyme," The Journal of Biological Chemisty, 238(8):2698-2707 (1963).
Chandler, J. P., "Purification and characterization of antibodies," pp. 125-155 (2006).
Doherty, E. A. S. et al., "Microchannel wall coatings for protein separations by capillary and chip electrophoresis," Electrophoresis, 24(1-2):34-54 (2003).
Dolnik, V., "Capillary electrophoresis of proteins," Electrophoresis, 26:1-16 (2005).
Engvall, E. et al., "Enzyme-linked immunosorbent assay (ELISA). Quantitative assay of immunoglobulin G," Immunochemistry, 8(9):871-874 (1971).
Fermani, S. et al., "Protein crystallization on polymeric film surfaces," Journal of Crystal Growth, 224(3-4):327-334 (2001).
Fleming, S. A., "Chemical reagents in photoaffinity labeling," Tetrahedron, 51(46):12479-12520 (1995).
Fouque, B. et al., "Light directed assembly of micro array in a glass capillary," Abstracts of the 7th International Conference on Miniaturized Chemical and Biochemical Analysis Systems, Oct. 5-9, 2003, Squaw Valley, CA., USA.
Hartree, E. F., "Determination of protein: a modification of the Lowry method that gives a linear photometric response," Anal. Biochem., 48:422-427 (1972).
Herr, A. E., et al., "On-chip coupling of isoelectric focusing and free solution electrophoresis for multidimensional separations," Anal. Chem., 75(5):1180-1187 (2003).
Horvath, J. et al., "Polymer wall coatings for capillary electrophoresis," Electrophoresis, 22:644-655 (2001).
Hogue-Angeletti, R., "Design of useful peptide antigens," Journal of Biomolecular Techniques, 10:2-10 (1999).
Hu, S. et al., "Surface modification of poly(dimethylsiloxane) microfluidic devices by ultraviolet polymer grafting," Analytical Chemistry, 74(16):4117-4123 (2002).
Jalal Zohuriaan-Mehr, M., "Advances in chitin and chitosan modification through graft copolymerization: a comprehensive review," Iranian Polymer Journal, 14(3):235-265 (2005).
Jiang, T. et al., "The synthesis and characterization of a pyridine-linked cyclodextrin dimer," J. Org. Chem., 59(18):5149-5155 (1994).
Khandurina, J. et al., "Micromachined capillary cross-connector for high-precision fraction collection," Journal of Chromatography A, 979(1-2):105-113 (2002).
Khandurina, J. et al., "Micropreparative fraction collection in microfluidic devices," Anal. Chem., 74(7):1737-1740 (2002).
Kaniansky, D. et al., "Capillary electrophoresis Separations on a planar chip with the column-coupling configuration of the separation channels," Anal. Chem., 72(15):3596-3604 (2000).
Kraus, R. et al., Wochenscher, 10:736 (1897).
Kuhn, R. et al., Capillary Electrophoresis Principles and Practice, Springer Laboratory, Berlin Heidelberg, Germany (1993), 383 pages.
Layne, E., "Spectrophotometric and turbidimetric methods for measuring proteins," Methods in Enzymology, 3:447-454 (1957).
Lowry, O. H. et al., "Protein measurement with the folin phenol reagent," J. Biol. Chem., 193:265-275 (1951).
Lalwani, S. et al., "Alkali-stable high-pI isoelectric membranes for isoelectric trapping separations," Electrophoresis, 25(14):2128-2138 (2004).
Muller, O. et al., "Design of a high-precision fraction collector for capillary electrophoresis," Anal. Chem., 67(17):2974-2980 (1995).
Pritchett, T. J.: "Review: Capillary isoelectric focusing of proteins," Electrophoresis, 17(7):1195-1201 (1996).
Rebmann, V. et al., "Biochemical analysis of HLA-DP gene products by isoelectric focusing and comparison with cellular and molecular genetic typing results," Exp. Clin. Immunogenet., 12(1):36-47 (1995).
Rocklin, R. D. et al., "A microfabricated fluidic device for performing two-dimensional liquid-phase separations," Anal. Chem., 72(21):5244-5249 (2000).
Rooseboom, M. et al., "Enzyme-catalyzed activation of anticancer prodrugs," Pharmacological Reviews, 56(1):53-102 (2004).
Rybicki, E. P. et al., "Enzyme-assisted immune detection of plant virus proteins electroblotted onto nitrocellulose paper," Journal of Virological Methods, 5(5-6):267-278 (1982).
Scatchard, G., "The attractions of proteins for small molecules and ions," Ann. N.Y. Acad. Sci., 51:660-672 (1949).
Sharma, L. et al., "Quaternary amino sugars: Synthesis and characterization of quaternary ammonium salts of N-substituted derivatives of 6-amino-6-deoxy-1,2-O-isopropylidene-α-D-glucofuranose," Indian Journal of Chemistry, 33B:851-854 (1994).
Smith, P. K. et al., "Measurement of protein using bicinchoninic acid," Analytical Biochemistry, 150(1):76-85 (1985).
Stibler, H. et al., "Quantitative estimation of abnormal microheterogeneity of serum transferrin in alcoholics," Pharmacolology Biochemistry & Behavior, 13(1):47-51 (1980).
Thiele, C. et al., "Photoaffinity labeling of central cholecystokinin receptors with high efficiency," Biochemistry, 32(11):2741-2746 (1993).
Towbin, H. et al., "Electrophoretic transfer of proteins from polyacrylamide gels to nitrocellulose sheets: procedure and some applications," Proc. Nat. Acad. Sci. USA, 76(9):4350-4354 (1979).
Van Weemen, B. K. et al., "Immunoassay using antigen-enzyme conjugates," FEBS Letters, 15(3):232-236 (1971).
Wakankar, A. et al., "Analytical methods for physicochemical characterization of antibody drug conjugates," Landes Bioscience, 3(2):161-172 (2011).
Xu, W. L. et al., "Synthesis of chitosan quaternary ammonium salts," Chinese Chemical Letters, 12(12):1081-1084 (2001).
Xin, Y. et al., "Isoelectric focusing/western blotting: A novel and practical method for quantitation of carbohydrate-deficient transferrin in Alcoholics," Alcoholism: Clinical and Experimental Research, 15(5):814-821 (1991).
Yalow, R. S. et al., Immunoassay of endogenous plasma insulin in man, J. Clin. Invest., 39(7):1157-1175 (1960).
Zuckermann, R. N. et al., "Discovery of nanomolar ligands for 7-transmembrane G-protein-coupled receptors from a diverse N-(substituted)glycine peptoid library," J. Med. Chem., 37:2678-2685 (1994).
Office Action for European Application No. 05774933,5, mailed Feb. 14, 2013, 3 pages.
Notice of Reasons for Rejection for Japanese Application No. 2011-148034, mailed Apr. 16, 2013, 4 pages.
Office Action for U.S. Appl. No. 12/950,660, mailed May 1, 2014.
Office Action for U.S. Appl. No. 12/950,660, mailed Jul. 17, 2013.
Office Action for U.S. Appl. No. 12/950,660, mailed Dec. 28, 2012.
Office Action for U.S. Appl. No. 13/092,595, mailed Jul. 17, 2013.
Office Action for U.S. Appl. No. 13/092,595, mailed Apr. 24, 2014.

(56) References Cited

OTHER PUBLICATIONS

International Preliminary Report on Patentability for International Application No. PCT/US2006/036808, dated Mar. 26, 2008, 6 pages.
International Preliminary Report on Patentability for International Application No. PCT/US2006/013447, dated Oct. 9, 2007, 6 pages.
International Preliminary Report on Patentability for International Application No. PCT/US2008/072927, dated Feb. 24, 2010, 8 pages.
Office Action for U.S. Appl. No. 13/778,757, mailed May 9, 2014.
European Search Report for European Application No. 13183395.6, mailed Mar. 4, 2014, 7 pages.
Office Action for U.S. Appl. No. 12/358,724, mailed Oct. 14, 2011.
Office Action for U.S. Appl. No. 12/358,724, mailed Aug. 29, 2012.
Office Action for U.S. Appl. No. 12/358,724, mailed Jul. 1, 2013.
Office Action for U.S. Appl. No. 12/358,724, mailed Dec. 31, 2013.
International Search Report and Written Opinion for International Application No. PCT/CA2013/050304, mailed Jul. 24, 2013, 9 pages.
Office Action for U.S. Appl. No. 11/827,098, mailed Apr. 3, 2012.
Office Action for U.S. Appl. No. 11/827,098, mailed Nov. 1, 2010.
Office Action for U.S. Appl. No. 11/827,098, mailed Apr. 20, 2010.
Office Action for U.S. Appl. No. 13/573,799, mailed Mar. 27, 2014.
Office Action for U.S. Appl. No. 13/097,285, mailed Apr. 23, 2013.

* cited by examiner protected, resin-bound peptide generated by SPPS labeled resin-bound peptide fully deprotected free peptide pI standard

ELECTROPHORESIS STANDARDS, METHODS AND KITS

CROSS REFERENCE TO RELATED APPLICATIONS

This application claims the benefit of, and priority to, U.S. Provisional Patent Application Ser. No. 60/719,246, filed on Sep. 20, 2005, the entire disclosure of which is hereby incorporated by reference. This application is related to U.S. patent application Ser. No. 11/401,699 titled Automated Micro-Volume Assay System, filed on Apr. 10, 2006, and U.S. patent application Ser. No. 11/185,247 titled Methods and Devices for Analyte Detection, filed on Jul. 19, 2005, the entire disclosure of both of which are hereby incorporated by reference.

TECHNICAL FIELD

The present invention relates in general to electrophoresis separation, and more particularly to electrophoresis standards, methods and kits for any one or more of detecting, quantifying and/or characterizing analytes.

INTRODUCTION

Electrophoresis is a technique for separating mixtures of molecules based on their different rates of travel in electric fields. Common modes of electrophoretic separations include separating molecules based on differences in their mobilities in a buffer solution i.e. zone electrophoresis, in a gel or polymer solution i.e. gel electrophoresis, or in a pH gradient i.e. isoelectric focusing. The movement of molecules during electrophoresis can be highly variable, making interpretation dependent upon a comparison to electrophoresis standards, whose behavior has been characterized.

The mobility of an ion is defined as the coefficient of proportionality between the electrophoretic velocity of the ion and the applied electric field as in equation 1 below:

$$v = \mu E \quad (1)$$

where v is the velocity of the analyte, $\mu$ is the mobility of the analyte and E is the electric field strength. The mobility itself is dependent on the nature of the molecule and the solvent surrounding it as in equation 2 below:

$$\mu = q/f \quad (2)$$

where q is the net charge of the analyte molecule and f is the coefficient of friction of the analyte molecule.

Zone electrophoresis is typically performed in a buffer of single pH, so mobilities of analytes are determined by the charge and frictional coefficient of the analyte in a separation buffer. In gel electrophoresis, the mobility of the analytes are further modified, for example, by a the polymer gel, which decreases the mobilities of the analytes. Isoelectric focusing takes place in a gradient of pH, so that analytes containing both acid and base moieties, otherwise known as amphoteres, will have a net charge and hence, mobility defined in equation 2 varies with their position in the separation axis. In isoelectric focusing, the amphoteric analytes will focus at the position in the separation axis where their electrophoretic mobility is zero. The net charge as a function of pH is determined by the pKs of acid and base moieties in the analyte molecule.

Electrophoresis standards are important tools in biological and industrial applications. Electrophoresis standards include, for example, molecular weight (MW) standards in SDS polyacrylamide gel electrophoresis (PAGE), DNA size standards in agarose gels, and pI standards used in isoelectric focusing (IEF). Although many electrophoresis standards have been developed, there is still a great need to find new standards that can be used to detect, quantifying and/or characterize a wide variety of analytes.

For example, electrophoresis standards used in isoelectric focusing (IEF) are of importance. Proteins have been separated and analyzed by IEF for decades. In IEF a pH gradient is generated by placing a series of zwitterionic molecules called carrier ampholytes in an electric field. A protein of interest migrates through this gradient as long as it has a net charge. Negatively charged molecules will migrate through the pH gradient toward the anode (and acid pH) until it reaches a point where it has picked up enough protons to become neutral, at the molecules pI. If the molecule diffuses further toward the anode it will move into a region of lower pH and become positive charged, at which point the electric field will mobilize it back toward the cathode (and a higher pH) until it is once again neutralized. The converse is true if the protein started out positively charged. In this way molecules can be focused within a pH gradient at the point where they have a net neutral charge their so called isoelectric point. Although computer algorithms exist to predict the pIs of proteins these give varying results. They do not take into account perturbations on an ionizable group's pKa due to neighboring ionizable groups. These groups can be nearby in the primary sequence or in tertiary structure. Examples of programs include ProtParam and Compute pI/Mw. The pI of a protein can be determined directly in IEF PAGE gels using a pH meter with a microprobe or by comparison to another molecule whose pI is known.

In addition, electrophoresis standards are important in Western Blotting techniques (also referred to as "Western Blots" or "Westerns"). Western Blotting is a technique well known to molecular biologists (see Towbin, H., Staehelin, T., Gordon, J. *Proc. Nat. Acad. Sci. U.S.A.* 76 (1979), 4350-4354) Briefly, proteins are separated through a matrix, usually a polyacrylamide gel, and then transferred to a solid support such as a nitrocellulose filter. The location of a specific protein of interest is identified by probing the filter with antibodies to that protein. These antibodies are then themselves probed with secondary antibodies conjugated to detection molecules. Often the method of detection is chemiluminescence. Generally the separation mode is by molecular weight, but IEF can also be used.

Isoelectric focusing Western Blots are know in the art (see Rebmann V, Kubens B S, Ferencik S, Grosse-Wilde H., *Exp Clin Immunogenet* 1995; 12(1):36-47) but are very difficult to perform consistently. Prepackaged IEF gels are commercially available; however they are not typically used in Western Blots. One hurdle is that the gels are exceedingly fragile due to their low acrylamide concentration.

Isoelectric focusing is often performed within capillaries and multiple commercial instruments exist that perform this protocol. (see Wehr T, Zhu M, Rodriguez-Diaz R, Capillary isoelectric focusing. Methods Enzymol. 1996; 270:358-74.) Several commercial instruments capable of performing this procedures are available from vendors including the PA/ACE, Paragon, and ProteomeLab product lines of instruments from Beckman Coulter, the Agilent Capillary Electrophoresis system, and the iCE280 Analyzer from Convergent Biosciences. However, it is only very recently that technology has been developed to perform a Western blotting technique within a capillary as described in co-pending U.S. patent application Ser. No. 11/185,247 and U.S. Provisional Patent Application Ser. No. 60/669,694 the entire disclosures of which are hereby incorporated by reference.

Large proteins (>15 KDa) are typically used as IEF standards. However, these proteins are difficult to manufacture, purify, label, and store. This has driven the development of peptide chemistries for use IEF standards (see Cruickshank, K. A., J. Olvera, U. R. Muller. Simultaneous Multiple Analyte Detection Using Fluorescent Peptides and Capillary Isoelectric Focusing. 1998. *J. Chromatogr. A.* 817: 41-47; Shimura, K., K. Kamiya, H. Matsumoto, K. Kasai. Fluorescence-Labeled Peptide pI Markers for Capillary Isoelectric Focusing. 2002. *Anal. Chem.* 74: 1046-1053). However peptides are small, and can pass right through nitrocellulose filters and are poorly captured in devices, such as capillaries. Similar issues exist for the use of molecular weight and other charge/mass standards that one wished to immobilize within capillaries or on solid supports, making it desirable to develop chemistries that enable the immobilization of electrophoresis standards. Thus, further developments are needed.

SUMMARY

In summary, the present invention relates generally to electrophoresis separation, and more particularly to electrophoresis standards, methods and kits for any one or more of detecting, quantifying and/or characterizing analytes.

In some embodiments provided herein are electrophoresis standards, methods and kits useful for, among other things, any one or more of detecting, quantifying and/or characterizing analytes. In an illustrative embodiment, electrophoresis standards comprise one or more moieties capable of affecting electrophoretic mobility, capable of detection, and capable of immobilizing the standard. In some embodiments, the electrophoresis standard comprises a one or more moieties capable of immobilizing the standard by covalently linking the standard to a substrate.

In one aspect, the invention provides an electrophoresis standard comprising: a compound comprised of one or more moieties, at least one of said moieties being comprised of one or more reactive moieties, wherein the reactive moieties, when activated, attach the electrophoresis standard to a substrate.

In another aspect, embodiments of the present invention provides methods of making the electrophoresis standards described herein. In some embodiments, the method comprises synthesizing a molecule comprising an acidic domain comprising one or more ionizable groups and a basic domain comprising one or more ionizable groups. In some embodiments, the method is used for the synthesis of a plurality of electrophoresis standards with different isoelectric points.

In further aspects, embodiments provide methods of detecting, quantifying and/or characterizing an analyte using electrophoresis standards described herein. In exemplary embodiments, methods comprise the steps of: resolving an analyte and an electrophoresis standard in an electrophoretic field, immobilizing the electrophoresis standard, and comparing the analyte to the standards. Also provided are methods of determining the isoelectric point or the analyte using the electrophoresis standards described herein. In some embodiments, the method comprises forming a pH gradient in a fluid path comprising one or more analytes and one or more electrophoresis standards, focusing, immobilizing, detecting, and determining the isoelectric point of one or more analytes by comparing one or more signals of the one or more analytes to one or more signals of the one or more standards.

BRIEF DESCRIPTION OF THE FIGURES

These and various other features and advantages of the present invention will be apparent upon reading of the following detailed description in conjunction with the accompanying drawings and the appended claims provided below. The skilled artisan will understand that the figures, described below, are for illustration purposes only. The figures are not intended to limit the scope of the present teachings in any way.

DETAILED DESCRIPTION OF EMBODIMENTS

Figure 1:
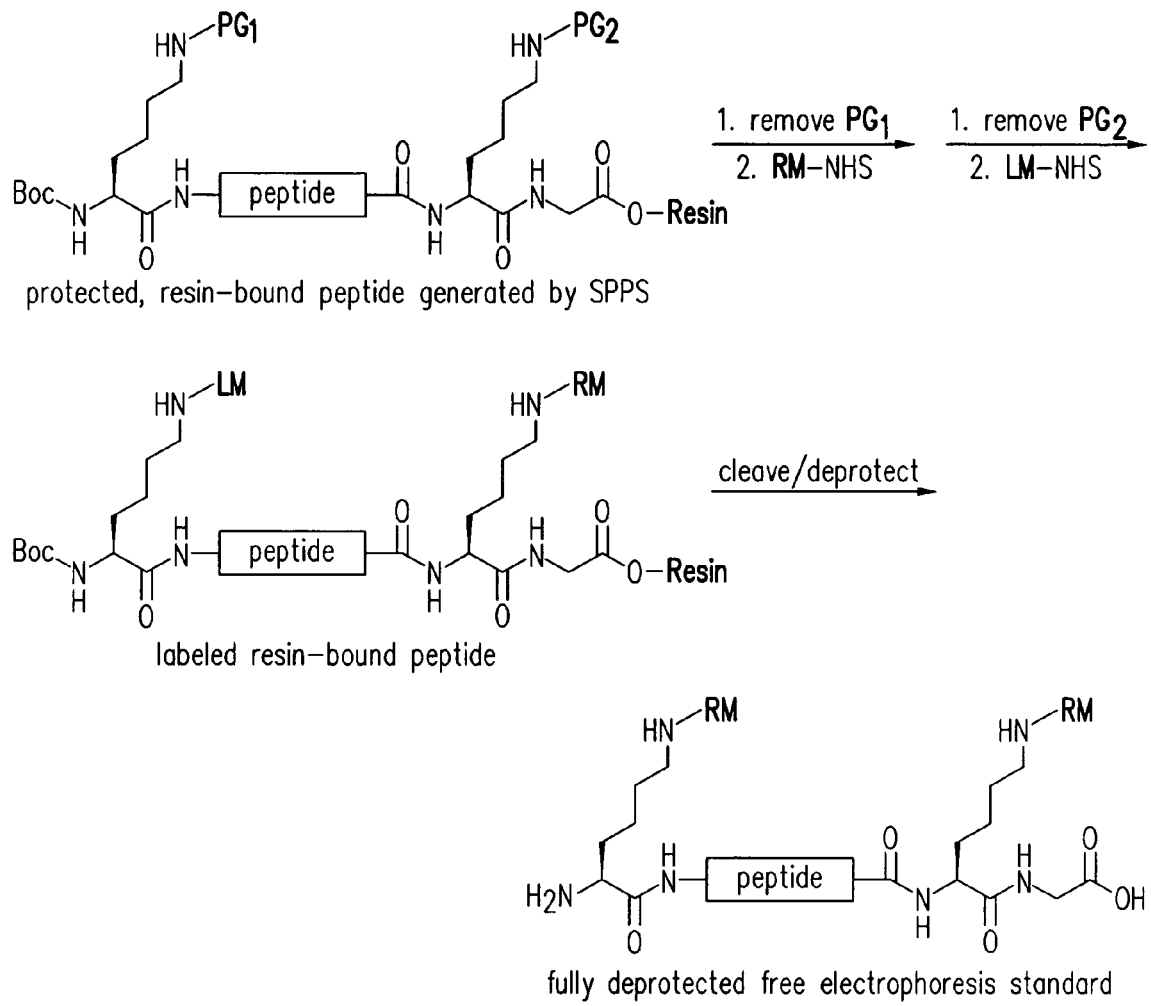
FIG. 1 illustrates an exemplary synthesis scheme of an electrophoresis standard according to embodiments of the present teaching.
Figure 1:
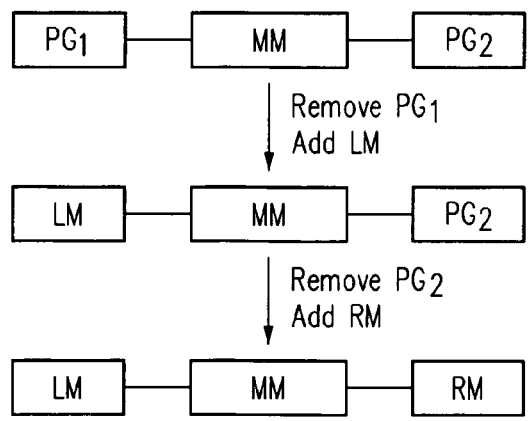

In summary, the present invention relates generally to electrophoresis separation, and more particularly to electrophoresis standards, methods and kits for any one or more of detecting, quantifying and/or characterizing analytes.

Electrophoresis Standards Compositions

Provided herein are compositions useful for, among other things, electrophoresis standards. Electrophoresis standards of the present invention are useful for any or more of: detecting, quantifying and/or characterizing analytes. In exemplary embodiments, electrophoresis standards are generally comprised of: one or more moieties capable of affecting electrophoretic mobility, capable of detection, and capable of immobilizing the standard. In some embodiments, the electrophoresis standard comprises one or more moieties capable of immobilizing the standard by covalently linking the standard to a substrate. Typically, the one or more moieties includes one or more functional groups configured to exhibit or perform the desired functionality.

In one embodiment, the invention provides an electrophoresis standard comprising: a compound comprised of one or more moieties, at least one of said moieties being comprised of one or more reactive moieties, wherein the reactive moieties, when activated, attach the electrophoresis standard to a substrate.

In some embodiments, the invention provides electrophoresis standards having a general formula of:

LM-MM-RM where LM is one or more label moieties, MM is one or more mobility moieties and RM is one or more reactive moieties, and as described in detail below.

In other embodiments, the electrophoresis standard further comprises one or more mobility moieties. The mobility moiety can comprise any entity capable of affecting electrophoretic mobility of the standard. The electrophoretic mobility of the entire compositions can be largely dominated by the properties of the mobility moiety. Properties of the mobility moiety that can affect electrophoretic mobility include, but are not limited to, molecular weight, charge to mass ratio, pI, and hydrophobicity.

The mobility moiety can be any organic and/or inorganic molecule, synthetic or naturally-occurring monomer, oligomer or polymer and any combinations thereof. In some embodiments, the mobility moiety can be an amino acid, peptide, oligopeptide, protein, nucleotide, polynucleotide, carbohydrate, polysaccharide, lipid, ampholyte, dye, heterocycles, and any combinations thereof.

In some embodiments, the electrophoresis standard comprises from 1 to 1000 or more amino acids. The amino acids can be L-amino acid, D-amino acid, an amino acid analog and any combinations thereof. In some embodiments, the standard comprises a modified amino acid. The modified amino acid can make the standard resistant to proteolysis.

The electrophoresis standards comprise one or more label moieties (LM) capable of detection. The label moiety, as will be appreciated by those in the art, can encompass a wide variety of possible labels. In general, labels include, optical dyes, including colored or fluorescent dyes; chemiluminescent labels, phosphorescent labels, enzymatic labels such as alkaline phosphatase and horseradish peroxidase, bioluminescent labels, isotopic labels, which may be radioactive or heavy isotopes, mass labels and particles such as colloids, magnetic particles, etc.

In some embodiments, the label moiety can be a single isomer dye. In some embodiments, the label moiety comprises a fluorescent dye. The fluorescent dye can comprise any entity that provides a fluorescent signal and that can be used in accordance with the methods and devices described herein. Typically, the fluorescent dye comprises a resonance-delocalized system or aromatic ring system that absorbs light at a first wavelength and emits fluorescent light at a second wavelength in response to the absorption event. A wide variety of such fluorescent dye molecules are known in the art. For example, fluorescent dyes can be selected from any of a variety of classes of fluorescent compounds, non-limiting examples include xanthenes, rhodamines, fluoresceins, cyanines, phthalocyanines, squaraines, bodipy dyes, coumarins, oxazines, and carbopyronines. In some embodiments, the fluorescent dye is 5-carboxytetramethylrhodamine (5-TAMRA).

The electrophoresis standards comprise one or more reactive moieties (RM). In some embodiments the reactive moieties are capable of immobilizing the standard. Immobilization may be accomplished by a variety of methods. For example, in some embodiments, the electrophoresis standards comprise one or more reactive moieties capable of covalently linking the standards to a substrate. In this example, activation of the reactive moieties covalently links the standard to substrate relative to the analyte of interest so that standard and analyte can be compared. In some embodiments, the standard comprises two or more reactive moieties. In embodiments employing two or more reactive moieties, each reactive moiety can be the same, or some or all of the reactive moieties may differ. Having two or more reactive moieties can increase immobilization of the standard by increasing the number of bonds between the standard and a substrate. For example, it can be desirable to increase the immobilization efficiency of the standard in a capillary IEF.

A wide variety of reactive moieties suitable for covalently linking two molecules together are well-known; however such reactive moieties have not been synthesized in combination with other moieties to form the compositions of the present invention. The actual choice of reactive moieties will depend upon a variety of factors, and will be apparent to those of skill in the art based on the teaching of the present invention herein. For example, the reactive moiety can bind to carbon-hydrogen (C—H) bonds of proteins. Since many separation media also contain components with C—H bonds, compounds that react with sulfhydryl (S—H) groups may be advantageous in that S—H groups are found uniquely on proteins relative to most separation media components. Compounds that react with amine or carboxyl groups may also be advantageous due to the prevalence of such groups on proteins.

Suitable reactive moieties (RM) include, but are not limited to, photoreactive groups, chemical reactive groups, and thermoreactive groups.

When the reactive moiety is comprised of one or more photoreactive groups, in some embodiments the photoreactive groups are comprised of one or more latent photoreactive groups that upon activation by an external energy source, forms a covalent bond with other molecules. A list of suitable latent photoreactive groups are described in U.S. Pat. Nos. 5,002,582 and 6,254,634, the disclosures of which are incorporated herein by reference. These photoreactive groups generate active species such as free radicals and particularly nitrenes, carbenes, and excited states of ketones upon absorption of electromagnetic energy. Additionally, photoreactive groups can be chosen that are responsive to various portions of the electromagnetic spectrum, such as those responsive to ultraviolet, infrared and visible portions of the spectrum. For example, upon exposure to a light source, the photoreactive group can be activated to form a covalent bond with an adjacent molecule.

Suitable photoreactive groups include, but are not limited to, aryl ketones, azides, diazos, diazirines, and quinones.

In some embodiments, the photoreactive group comprises aryl ketones, such as benzophenone, acetophenone, anthraquinone, anthrone, and anthrone-like heterocycles or their substituted derivatives. Benzophenone is a preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom to create a radical pair. The subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source.

In other embodiments, photoreactive groups are comprised of azides, such as arylazides such as phenyl azide, 4-fluoro-3-nitrophenyl azide, acyl azides such as benzoyl azide and p-methylbenzoyl azide, azido formates such as ethyl azidoformate, phenyl azidoformate, sulfonyl azides such as benzenesulfonyl azide, and phosphoryl azides such as diphenyl phosphoryl azide and diethyl phosphoryl azide.

Photoreactive groups may also be comprised of diazo compounds and includes diazoalkanes such as diazomethane and diphenyldiazomethane, diazoketones such as diazoacetophenone and 1-trifluoromethyl-1-diazo-2-pentanone, diazoacetates such as t-butyl diazoacetate and phenyl diazoacetate, and beta-keto-alpha-diazoacetates such as t-butyl alpha diazoacetoacetate.

In further embodiments, photoreactive groups are comprised of diazirines such as 3-trifluoromethyl-3-phenyldiazirine, and photoreactive group comprises ketenes such diphenylketene.

In yet further embodiments, photoreactive groups are comprised of N-((2-pyridyldithio)ethyl)-4-azidosalicylamide, 4-azido-2,3,5,6-tetrafluorobenzoic acid, 4-azido-2,3,5,6-tetrafluorobenzyl amine, benzophenone-4-maleimide, benzophenone-4-isothiocyanate, or 4-benzoylbenzoic acid.

As described above, in embodiments employing two or more reactive moieties, each reactive moiety can be the same, or some or all of the reactive moieties may differ. For example, electrophoresis standards of the invention can comprise a photoreactive group (RM1) and a chemically reactive group (RM2). In some embodiments, electrophoresis standards are comprised of different photoreactive groups, non limiting examples include, two photoreactive groups of benzophenone and 4-azido-2,3,5,6-tetrafluorobenzoic acid (ATFB).

In addition to the use of photoactivatable chemistry described above, the reactive moieties may be comprised of chemical reactive groups, thermoreactive groups, and combinations thereof.

In some embodiments, the reactive moiety (RM) comprises a functional group that is configured to attach the standard to a substrate by forming a covalent linkage with a complementary group present on a substrate. Pairs of complementary groups capable of forming covalent linkages are known in the art and can be selected given the teaching of the present invention. In some embodiments, the substrate is formed of a material that comprises a nucleophilic group and the reactive group comprises an electrophilic group. In other embodiments, the reactive group comprises a nucleophilic group and the substrate is comprised of a material that comprises an electrophilic group. Complementary nucleophilic and electrophilic groups, or precursors thereof that can be suitably activated, useful for forming covalent linkages stable in assay conditions can be used. Examples of suitable complementary nucleophilic and electrophilic groups, as well as the resultant linkages formed there from, are described in U.S. Pat. No. 6,348,596, which is incorporated herein by reference.

Electrophoresis standards of the present invention may be synthesized to exhibit a broad range of characteristics and mobilities. In some embodiments, electrophoresis standards exhibit an isoelectric point in the range of about pH 2 to about pH 12. In some embodiments, electrophoresis standards have a molecular weight in the range of about 20 Da to about 800 kDa.

Methods

In another aspect of the present invention, methods of making electrophoresis standards are provided. In some embodiments, the method comprises synthesizing an electrophoresis standard comprised of one or more moieties capable of affecting electrophoretic mobility, capable of detection, and capable of immobilizing the standard. In some embodiments, the electrophoresis standard comprises one or more moieties capable of immobilizing the standard by covalently linking the standard to a substrate.

In some embodiments the method comprises the steps of: providing a mobility moiety with one or more protecting groups, and replacing the protecting groups with one or more label moieties and one or more reactive moieties. One example of the method is illustrated in the synthesis scheme shown in FIG. 1, where the protecting group(s) is generally shown as PG1 and PG2, the label moieties are shown as LM and the reactive moieties are shown as RM.

In some embodiments, peptide synthesis techniques are used to produce a resin bound peptide capped with a protecting group. In some embodiments the mobility moiety comprises the sequence lysine-peptide-lysine. The primary amines of the two lysines can be protected by two different protecting groups. The protecting groups can be sequentially removed from the lysines and replaced with the one or more label moieties and one or more and reactive moieties using chemical techniques well known top those in the art. The molecule is then cleaved from the resin and deprotected to produce the final electrophoresis standard.

Those skilled in the art will recognize that the modified lysines need not be terminal. However, placing them too close to each other can cause the reactive moiety to react with the label moiety upon induction, and may lower both capture and detection. Lysines are not the only amino acid that can be differentially labeled in this manner; another suitable example is cysteine. An exemplary synthesis scheme of an electrophoresis standards using a peptide as a mobility domain or mobility moiety is illustrated in Example 1 and FIG. 1.

In some embodiments, electrophoresis standards composition and methods of the present invention employ a polypeptide in which the label moiety is a fluorescent dye, for example, 5-carboxy-tetramethyl rhodamine (5-TAMRA) and a reactive moiety, for example, ATFB. In some embodiments, the peptide sequence is comprised of Lysines (K), Glycines (G), and Glutamatic Acid (E) residues. For example, the peptide Boc-K(Fmoc)GKEKEKEKGK(Mmt)G- is synthesized on an HMP resin using standard Fmoc chemistry. The Fmoc group is removed and with the resulting primary amine is labeled using ATFB-SE (4-azido-2,3,5,6-tetrafluorobenzoic acid, succinimidyl ester). The Mmt is then removed and the resulting primary amine is then reacted with 5-TAMRA-SE (5-carboxytetramethylrhodamine, succinimidyl ester). The peptide can be deprotected and cleaved from the resin and then purified by reverse-phase HPLC, lyophilized, and dissolved in water.

Figure 2:
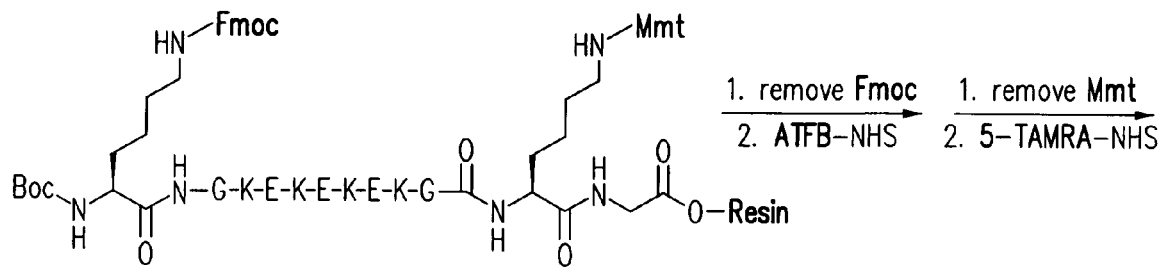
FIG. 2 illustrates an exemplary synthesis scheme of a electrophoresis standard comprising a peptide, 5-carboxy-tetramethyl rhodamine (5-TAMRA) and 4-azido-2,3,5,6-tetrafluorobenzoic acid (ATFB) according to embodiments of the present teaching.
Figure 2:
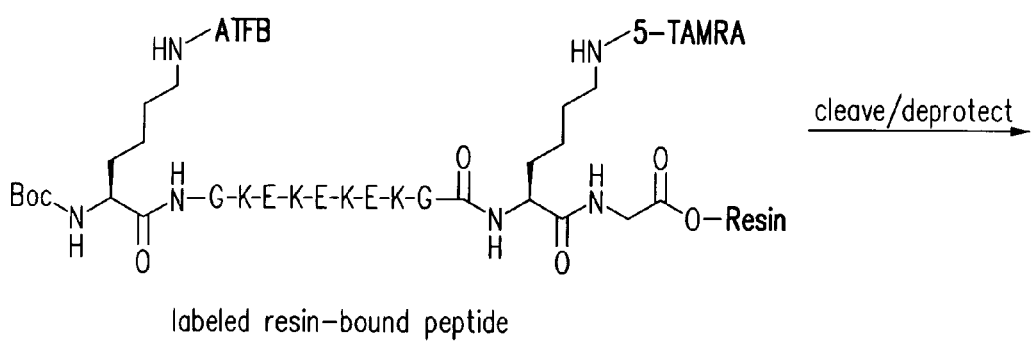
Figure 2:
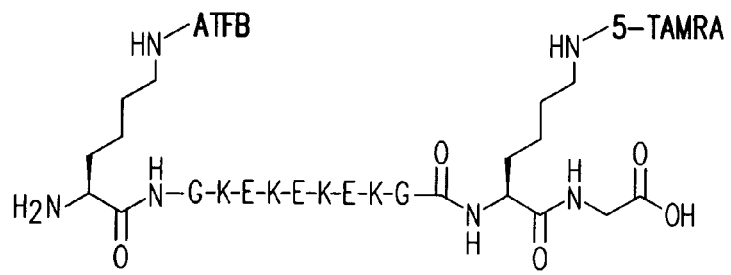

An exemplary synthesis scheme of an electrophoresis standard with a peptide mobility moiety, a fluorescent dye label moiety, and ATFB as the reactive moiety is illustrated in Example 2 and in FIG. 2.

Method of the present invention further comprise the steps of: providing a molecule with an acidic domain comprising one or more ionizable groups and molecule with a basic domain comprising one or more ionizable groups, and adding or removing one or more ionizable groups. In some embodiments, the method further comprises attaching one or more reactive moieties and/or one or more label moieties to the molecule. This method is suitable for the synthesis of a plurality of electrophoresis standards with different isoelectric points.

Of particular advantage, the teaching of the present invention allows for the selective synthesis of electrophoresis standards depending on the desired application. This provides a significant tool. For example, in an exemplary embodiment the mobility moiety can be configured to vary depending upon the desired mobility of the electrophoresis standard. For example, to produce selected molecular weight standards one would synthesize peptides of a desired length. The mobility moiety can be based upon peptides of known sequence to achieve the desired performance. For example, small peptides can be ligated to other small peptides or purified proteins to build standards of varying size. Techniques exist for labeling proteins produced in-vivo or in-vitro.

By altering the number of acidic and basic amino acids of the primary peptide sequence will alter the performance of pI standards. Although computer algorithms exist to predict the pIs of proteins these give varying results. They do not take into account perturbations on an ionizable group's pKa due to neighboring ionizable groups. These groups can be nearby in the primary sequence or in tertiary structure. Examples of programs include ProtParam and Compute pI/Mw. The pI of standards can be determined directly in IEF PAGE gels using a pH meter with a microprobe.

According to teachings of the present invention, a gamut of peptides with varying isoelectric focusing points can be synthesized as desired. The method makes use of the effect that ionizable groups have one other ionizable groups that are nearby either in secondary sequence or through 3-dimensional space, which are here referred to as proximity effects. One example of a proximity effect occurs in citric acid, which contains 3 carboxylic acid groups. The pKa is 3.15 for the first ionization, 4.77 for the second, and 5.17 for the third. The second pKa is higher than the first because ionization of the second acid group generates a second negative charge, a process which is unfavorable due to repulsion by the pre-existing negative charge. Similarly the third ionization has an even higher pKa because it generates a third negative charge, which is repelled by two pre-existing negative charges. Another example of this effect is seen in diethylenetriamine, containing three amino groups, in which ionization of these groups generates positive charges. In this case each successive ionization event occurs at successively lower pKa's due to repulsion between increasing numbers of positive charges: $pKa1=10.02$, $pKa2=9.21$, $pKa3=4.42$. Conversely, charges of opposite sign can stabilize each other when close to each other, such that the effective pKa of a carboxylic acid group is lowered, and that of a nearby amino group is raised. This occurs, for example, in the amino acid glycine, with pKa's of 2.3 and 9.6 vs. pKa's of 3.6 and 7.6 for the isolated carboxylic acid and amino groups, respectively.

Molecules with acidic and basic ionizable groups have a pI value, which is the pH at which the net charge on the molecule is zero. The amphotere glycine, having one carboxylic acid and one amino group, is an example. Even though it has a pI of approximately 5.97, it has a broad pH range over which it is nearly neutral, however, due to the large gap between its two pKa's. In other words, it does not have much charge over a broad pH range, and may be less preferred as a pI standard. To generate pI standards that forms a sharp band in a pH gradient under electrophoretic conditions, the value of pI-pKa is preferably less than 1.5 (see Righetti, et. al. *J. Cap. Elec.*, 004:2, 1997, 47-59). This condition ensures sufficient charge is present on the electrophoresis standard as it approaches the pH value corresponding to its pI, and its resulting electrophoretic velocity can effectively counteract diffusion in the opposite direction. Meeting this condition requires the presence of basic and acidic ionizable groups with pKa's near the desired pI. These pKa's can be generated in a systematic way using a single basic and acid ionizable group if the above described proximity effects are used. An exemplary synthesis scheme of an electrophoresis standards with different isoelectric points is illustrated in Example 3 below.

Peptide-based electrophoresis standards can be made according to method of the present invention that are resistant to proteolytic cleavage. For example, in one embodiment a peptide electrophoresis is synthesized of D-configuration amino acids (i.e. D-Lys (k) and D-Glu (e)). Other means of introducing protease resistance into a peptide pI standards include, but are not limited to, use of cyclic structures, inclusion of N-substituted residues (this group contains the specific example of peptoids, which are poly(N-substituted glycines)), peptide bond isosteres, modification of the N- and C-termini, and inclusion of unnatural or nonproteinogenic amino acid residues or linkers.

Also provided herein are methods of detecting an analyte using an electrophoresis standard. Detecting has its standard meaning, and is intended to encompass the detection, measurement, and characterization of an analyte. For example, an analyte can be detected, measured, and characterized by comparing the electrophoretic mobility of the analyte to an electrophoresis standard. The electrophoresis standards describe herein may be used for, among other things, determining the isoelectric point and molecular weight of an analyte of interest.

The analyte to be detected can be any analyte selected by the user. The analyte can comprise any organic or inorganic molecule capable of being detected. Non-limiting examples of analytes that can be detected include proteins, oligopeptides and peptides, derivatives and analogs, including proteins containing non-naturally occurring amino acids and amino acid analogs. Other example of analytes that can be detected include carbohydrates, polysaccharides, glycoproteins, viruses, metabolites, cofactors, nucleotides, polynucleotides, transition state analogs, inhibitors, drugs, nutrients, electrolytes, hormones, growth factors and other biomolecules as well as non-biomolecules, as well as fragments and combinations of all the forgoing.

The analyte may generate a signal capable of detection. In some embodiments, the analyte can be contacted with one or more detection agents. A detection agent is capable of binding to or interacting with the analyte to be detected. Contacting the detection agent with the analyte of interest can be by any method known in the art, so long as it is compatible with the methods described herein.

Detection agents comprise any organic or inorganic molecule capable of binding to interact with the analyte to be detected. Non-limiting examples of detection agents include proteins, peptides, antibodies, enzyme substrates, transition state analogs, cofactors, nucleotides, polynucleotides, aptamers, lectins, small molecules, ligands, inhibitors, drugs, and other biomolecules as well as non-biomolecules capable of binding the analyte.

In some embodiments, the detection agents comprise one or more label moieties. In embodiments employing two or more label moieties, each label moiety can be the same, or some, or all, of the label moieties may differ. In some embodiments detection is carried out via protein-protein interaction, such as a biotin/strepaviden or a epitope/antibody interaction. Typically, an analyte or electrophoresis standard is detected by detecting a signal from a label moiety. This technique includes, but is not limited, to detecting isotopic labels, immune labels, optical dyes, enzymes, particles and combinations thereof such as chemiluminescent labeled antibodies and fluorescent labeled antibodies.

In some embodiments, the method uses an electrophoresis standard comprising one or more moieties capable of affecting electrophoretic mobility, capable of detection, and capable of covalently linking the standard to a substrate.

Provided herein are methods of determining the mobility of one or more analytes. In some embodiments, the method comprises the steps of: providing one or more analytes and one or more electrophoresis standards in a fluid path, resolving the one or more analytes and the one or more standards, and detecting signals from the one or more analytes and the one or more standards, and comparing the signals from the one or more analytes to signals from the one or more standards.

As will be appreciated by those in the art, virtually any method of loading the analyte and/or electrophoresis standards in the fluid path may be performed. For example, material can be loaded into one end of the fluid path. In some embodiments, the material is loaded into one end of the fluid path by hydrodynamic flow. For example, in embodiments wherein the fluid path is a capillary, the sample can be loaded into one end of the capillary by hydrodynamic flow, such that the capillary is used as a micropipette. In some embodiments, the material can be loaded into the fluid path by electrophoresis, for example, when the fluid path is gel filled and therefore more resistant to hydrodynamic flow.

In some embodiments, the method comprises loading an analyte and a electrophoresis standard into the same fluid path. Mobility standards serve to calibrate separation of the analyte and electrophoresis standards with respect to isoelectric point, or for an alternative separation mode, with respect to molecular weight. In some embodiments, methods of the present invention comprise loading an analyte and an electrophoresis standard into different fluid paths, for example two parallel fluid paths.

The fluid path can comprise any structure that allows liquid or dissolved molecules to flow. Thus, the fluid path can comprise any structure known in the art, so long as it is compatible with the methods described herein. In some embodiments, the fluid path is a bore or channel through which a liquid or dissolved molecule can flow. In some embodiments, the fluid path is passage in a permeable material in which liquids or dissolved molecules can flow. In one example, embodiments of the present invention are carried out in a fluid path and system as describe in U.S. patent application Ser. No. 11/401, 699 titled Automated Micro-Volume Assay System, filed on Apr. 10, 2006, the entire disclosure of which is hereby incorporated by reference. In another example, embodiments of the present invention are carried out in a system as described in U.S. patent application Ser. No. 11/185,247 titled Methods and Devices for Analyte Detection, filed on Jul. 19, 2005, the entire disclosure of which is hereby incorporated by reference.

The fluid path comprises a substrate. A substrate is any material that allows the detection of the analyte or standard within the fluid path and allows for immobilizing the electrophoresis standards and analytes. The substrate comprises any convenient material, such as glass, plastic, silicon, fused silica, gels, nitrocellulose, polyvinylidene difluoride, absorbed or covalently bound polymer, or coated surface, and the like. In some embodiments, the method employs a plurality of substrates.

The fluid path can vary as to dimensions, width, depth and cross-section, as well as shape, being rounded, trapezoidal, rectangular, etc., for example. The fluid path can be straight, rounded, serpentine, or the like. As described below, the length of the fluid path depends in part on factors such as sample size and the extent of sample separation required to resolve the analyte or analytes of interest.

In some embodiments, the fluid path comprises a tube with a bore, such as a capillary. In some embodiments, the method employs a plurality of capillaries. Suitable sizes include, but are not limited to, capillaries having internal diameters of about 10 to about 1000 μm, although more typically capillaries having internal diameters of about 25 to about 400 μm can be utilized. Smaller diameter capillaries use relatively low sample loads while the use of relatively large bore capillaries allows relatively high sample loads and can result in improved signal detection.

The capillaries can have varying lengths. Suitable lengths include, but are not limited to, capillaries of about 2 to 20 cm in length, although somewhat shorter and longer capillaries can be used. In some embodiments, the capillary is about 3, 4, 5, or 6 cms in length. Longer capillaries typically result in better separations and improved resolution of complex mixtures. Longer capillaries can be of particular use in resolving low abundance analytes.

Generally, the capillaries are composed of fused silica, although plastic capillaries and PYREX (i.e., amorphous glass) can be utilized, among others. As noted above, the capillaries do not need to have a round or tubular shape, other shapes, can also be utilized.

In some embodiments, the fluid path is comprised of a channel. In some embodiments, the method employs a plurality of channels. The fluid path can be comprised of a channel in a microfluidic device. Microfluidic devices typically employ channels in a substrate to perform a wide variety of operations. The microfluidic devices can comprise one or a plurality of channels contoured into a surface of a substrate. The microfluidic device can be obtained from a solid inert substrate, and in some embodiments in the form of a chip. The dimensions of the microfluidic device are not critical, but in some embodiments the dimensions are in the order of about 100 μm to about 5 mm thick and approximately about 1 centimeter to about 20 centimeters on a side. Suitable sizes include, but are not limited to, channels having a depth of about 5 μm to about 200 μm, although more typically having a depth of about 20 μm to about 100 μm can be utilized. Smaller channels, such as micro or nanochannels can also be used, so long as it is compatible with the methods described herein.

In another embodiment, the fluid path comprises a gel. In some embodiments, the gel is capable of separating the components of the sample based on molecular weight. A wide variety of such gels are known in the art, a non-limiting example includes polyacrylamide gel.

Methods of the present invention generally comprise resolving one or more analytes and standards in the fluid path. A variety of methods of separating a mixture into two or more components are suitable, and may include, but are not limited to, various kinds of electrophoresis. As used herein, electrophoresis refers to the movement of suspended or dissolved molecules through a fluid or gel under the action of an electromotive force applied to electrodes in contact with the fluid or gel.

In some embodiments, the steps of resolving or separating comprises isoelectric focusing (IEF). In an electric field, a molecule will migrate towards the pole (cathode or anode) that carries a charge opposite to the net charge carried by the molecule. This net charge depends in part on the pH of the medium in which the molecule is migrating. One common electrophoretic procedure is to establish solutions having different pH values at each end of an electric field, with a gradient range of pH in between. At a certain pH, the isoelectric point of a molecule is obtained and the molecule carries no net charge. As the molecule crosses the pH gradient, it reaches a spot where its net charge is zero (i.e., its isoelectric point) and it is thereafter immobile in the electric field. Thus, this electrophoresis procedure separates molecules according to their different isoelectric points.

When resolving is by isoelectric focusing, an ampholyte reagent can be loaded into the fluid path. An ampholyte reagent is a mixture of molecules having a range of different isoelectric points. Typical ampholyte reagents are Pharmalyte™ and Ampholine™ available from Amersham Biosciences of Buckinghamshire, England. Ampholytes can be supplied at either end of the fluid path, or both, by pumping, capillary action, gravity flow, electroendosmotic pumping, or electrophoresis, or by gravity siphon that can extend continuously through the fluid path.

In some embodiments, the step of resolving comprises electrophoresis of a sample in a polymeric gel. Electrophoresis in a polymeric gel, such as a polyacrylamide gel or an agarose gel separates molecules on the basis of the molecule's size. A polymeric gel provides a porous passageway through which the molecules can travel. Polymeric gels permit the separation of molecules by molecular size because larger molecules will travel more slowly through the gel than smaller molecules.

Alternatively, the step of resolving comprises micellar electrokinetic chromatography (MEKC) of a sample. In micellar electrokinetic chromatography, ionic surfactants are added to the sample to form micelles. Micelles have a structure in which the hydrophobic moieties of the surfactant are in the interior and the charged moieties are on the exterior. The separation of molecules is based on the interaction of these solutes with the micelles. The stronger the interaction, the longer the solutes migrate with the micelle. The selectivity of MEKC can be controlled by the choice of surfactant and also by the addition of modifiers to the sample. Micellar electrokinetic chromatography allows the separation of neutral molecules as well as charged molecules.

Methods of the present invention further provide the step of immobilizing one or more resolved analytes in the fluid path. In some embodiments, the method comprise immobilizing one or more electrophoresis standards in the fluid path. In some embodiments, the method comprise immobilizing both the analyte the electrophoresis standards in the fluid path. As described above, suitable reactive moieties for immobilization include, but are not limited to, photoreactive groups, chemical reactive groups, and thermoreactive groups. The actual choice of reactive moieties will depend upon a variety of factors, and will be apparent to those of skill in the art.

As used herein, immobilizing refers to substantially reducing or eliminating the motion of molecules in the fluid path. Immobilization can be achieved via covalent bonds. For example, an electrophoresis standard comprising the photoactivatable reactive moiety ATFB, can be immobilized in a gel filled capillary by a ATFB-polyPEG matrix in the capillary upon exposure to UV light. In some embodiments, the immobilization can be achieved via non-covalent means such as by hydrophobic or ionic interaction. In some embodiments, the resolved analytes and/or standards are immobilized in the fluid path by isoelectric focusing.

In some embodiments, the fluid path comprises one or more reactive moieties. A reactive moiety can be used to covalently immobilize the resolved analyte or analytes in the fluid path. In some embodiments, one or more reactive moieties in the fluid path can be used to covalently immobilize the resolved electrophoresis standard in the fluid path. The reactive moiety can comprise any reactive group that is capable of forming a covalent linkage with a corresponding reactive group. Thus, the reactive moiety can comprise any reactive group known in the art, so long as it is compatible with the methods described herein. In some embodiments, the reactive moiety comprises a reactive group that is capable of forming a covalent linkage with a corresponding reactive group of an analyte of interest. In embodiments employing two or more reactive moieties, each reactive moiety can be the same, or some or all of the reactive moieties may differ.

The reactive moiety can be attached directly, or indirectly to the fluid path. In some embodiments, the reactive moiety is supplied in solution or suspension, and may form bridges between the wall of the fluid path and the molecules in the sample upon activation. The reactive moiety can line the fluid path or, in another embodiment, is present on a linear or cross-linked polymer in the fluid path. The polymer may or may not be linked to the wall of the fluid path before and/or after activation.

As described above, a wide variety of reactive moieties suitable for covalently linking two molecules together are known. Suitable reactive moieties include, but are not limited to, photoreactive groups, chemical reactive groups, and thermoreactive groups. The actual choice of reactive moieties will depend upon a variety of factors, and will be apparent to those of skill in the art given the teaching and description of the present invention.

Signals of the analytes and the electrophoresis standards are detected by any suitable method known in the art. For example, the detection method can depend on the analyte of interest and the label on the electrophoresis standard. and can depend on the choice of labels selected by the user. In some embodiments, signals of one or more analytes are detected by detection of a chemiluminescent signal. In some embodiments, signals of one or more analytes are detected by detection of a fluorescent signal. In other embodiments, signals of one or more standards are detected by detection of a chemiluminescent signal. In yet further embodiments, signals of one or more standards are detected by detection of a fluorescent signal. Additionally, signals of the one or more analytes and signals of the one or more standards may both be detected by fluorescent signals.

Signal detection can be performed by monitoring a signal using conventional methods and instruments, provided the signal is measurable by the detection system. Examples of suitable systems include, but are not limited to: photodetectors, array of photodetectors, charged coupled device (CCD) arrays, etc. For example, a signal can be a continuously monitored, in real time, to allow the user to rapidly determine whether an analyte is present in the sample, and optionally, the amount or activity of the analyte. In some embodiments, the signal can be measured from at least two different time points and additionally the signal can be monitored continuously or at several selected time points. Alternatively, the signal can be measured in an end-point embodiment in which a signal is measured after a certain amount of time, and the signal is compared against a control signal (sample without analyte), threshold signal, a standard curve, or the electrophoresis standard signal.

Typically, detecting the analyte comprises imaging the fluid path comprising one or more electrophoresis standards. In some embodiments, the entire length of the fluid path can be imaged. Alternatively, a distinct part or portion of the fluid path can be imaged. The amount of signal generated is not critical and can vary over a broad range. The only requirement is that the signal be measurable by the detection system being used. In some embodiments, a signal can be at least 2-fold greater than the background. In some embodiments, a signal between 2 to 10-fold greater than the background can be generated. In some embodiments, a signal can be more than 10-fold greater than the background.

Kits

In another aspect of the present invention kits for performing the methods described herein, and for analyte detection systems are provided. In one embodiment, the kit comprises materials for making the electrophoresis standards described herein. Additionally, one or more mobility moieties, one or more reactive moieties, one or more label moieties are provided. In some embodiments, the kit comprises one or more electrophoresis standards as described herein. In some embodiments, the kit further comprises electrophoresis standard comprising a peptide, one or more fluorescent dyes and one or more photoreactive groups. Additional materials can include, but are not limited, fluid paths, such as capillaries and microfluidic devices. In addition, buffers, polymeric or polymerizable materials, blocking solutions, and washing solutions can be provided. In some embodiments, the kit can further comprise reagents for the activation of a reactive moiety. These other components can be provided separately from each other, or mixed together in dry or liquid form.

EXAMPLES

A number of experiments have been conducted. The following examples, including prophetic examples are provided below for illustration purposes only, and are not intended to limit the invention in any way.

Example 1

Electrophoresis standards can be produced according to the general synthesis scheme shown in FIG. 1 according to one embodiment of the present invention. A starting molecule is synthesized with 2 different protecting groups $PG_1$ and $PG_2$. In this example $PG_1$ is removed first and is replaced with a label moiety LM. Then $PG_2$ is removed and replaced with the reactive moiety RM. The resulting molecules mobility is largely governed by the core mobility moiety MM, although it may be influenced by one or both of the LM and RM.

Example 2

Synthesis of a polypeptide in which the detection moiety is a fluorescent dye, 5-carboxy-tetramethyl rhodamine (5-TAMRA) and the capture moiety is ATFB is illustrated in FIG. 2 according to another embodiment of the present invention. The synthesis scheme depicted is similar to FIG. 1, using a specific peptide sequence, protecting groups and moieties. In this example the peptide sequence is composed entirely of Lysines (K), Glycines (G), and Glutamatic Acid (E) residues. The peptide Boc-K(Fmoc)GKEKEKEKGK(Mmt)G was synthesized on an HMP resin using standard Fmoc chemistry. The Fmoc group was removed by treatment with 20% piperidine in DMF, and the resin was rinsed several times with DMF. The peptide resin was treated with four equivalents of ATFB-SE (4-azido-2,3,5,6-tetrafluorobenzoic acid, succinimidyl ester, Toronto Research Chemicals Inc., North York, Ontario, Canada e) in DMF in the presence of DIEA for several hours, and the resin was then washed with DMF, methanol, DCM, and DCE. The resin was then treated with 1:2:7 (v/v) AcOH/TFE/DCE (4×15 min), then washed with DCE, DIEA, methanol, and DMF. The resin was treated with two equivalents of 5-TAMRA-SE (5-carboxytetramethylrhodamine, succinimidyl ester, AnaSpec, Inc. San Jose) in DMF containing DIEA for several hours, then the resin was washed with DMF and methanol, followed by DCM. The resin was deprotected and cleaved with 95:2.5:2.5 (v/v) TFA/TIS/$H_2O$ for several hours, and the peptide was precipitated with cold $Et_2O$. The peptide was purified by reverse-phase HPLC, lyophilized, and dissolved in water. The identity of the product was confirmed by mass spectrometry, and purity established by analytical reverse-phase HPLC and capillary IEF.

Example 3

In another example the synthesis is performed as described in Example 2 with the following difference. Benzophenone succinimide ester (BP-SE, Invitrogen,) is used in place of ATFB-SE to produce a standard with an alternative photoinducable capture moiety.

Example 4

In another example multiple standards are labeled with different detection so that they are chromatically distinct. A pI mobility standard with the sequence $H_2N$—K(ATFB)GAE-HHK(5-TAMRA)G-OH has a pI of approximately 5.45. A different standard with the sequence $H_2N$—K(ATFB)GAE-HHK(5-ROX)G-OH (where ROX is Rhodamine X, Invitrogen) has 6.39. These standards can be combined with an analyte and separated, captured and detected. If different chromatic filters are used the two standards can be distinguished from each other unambiguously.

There are many advantages to differential labeling. Often multiple standards are used in separations but if their identity is not distinct, mistakes can be made in assignment. For this reason the use of color coded standards has been used in the art. Examples of such standards are HiMArk Prestainsed Protein Standards from Invitrogen, Kaleidoscope Prestained Standards from Bio-Rad, and Chemichrome Ultimate from Sigma, however such standards are limited and none of the products have a reactive moiety attached to them and thus are not immobilized as taught by the present invention.

According to embodiments of the present invention, differential labeling is not limited to two different color dyes but rather includes any combination of detection moiety described. For example, one standard may be labeled with a fluorescent dye and another is detected by probing with a conjugated protein. Labeling methods include but are not limited to chemiluminescents, fluorescents, phosphorescents, isotopic labels, immune labels, enzymes, particles, protein-protein interactions, and protein-biotin interactions.

Example 5

A peptide was synthesized with the following sequence, according to the procedure of Example 1, except using Ac—K(Fmoc)-OH in place of Boc-K(Fmoc)-OH to incorporate the N-terminal residue: Ac—K(ATFB) KKKK-KAibAibEEEGG K(5-TAMRA)G-$NH_2$.

Aib is 2-aminoisobutyric acid, and serves to separate the blocks of acid and basic residues so that they do not influence each others pKa's, and also provides stiffness to prevent the acid and basic groups from coming together due to attraction of opposite charges. The blocks of lysine (K) and glutamic acid (E) residues contain basic and acidic ionizable groups at a variety of pKa values in keeping with the proximity effects described above. The K residues are expected to have pKa's of approximately 10, 8, 6, 4, and 2, whereas the E residues are expected to have pKa's of approximately 4.5, 6.5, and 8.5. The approximate expected net charge on the peptide at various pH values is then as follows: pH 11, −3; pH 10, −2.5; pH 9, −1.7; pH 8, −0.8; pH 7, +0.3; pH 6, +1.2; pH 5, +2.3; pH 4, +3.2; pH 3, +4, pH 2, +4.5; pH 1, +5. The peptide is expected to have a pI between 7 and 8, and has basic and acidic ionizable groups that possess pKa values within 1.5 pH units of this pI value. The peptide is therefore expected to be a useful pI standard that forms a tight band under electrophoretic conditions in a pH gradient. Additional standards of desired pIs can be generated by systematically varying the number of sequential K and E residues in a set of peptides based on the above sequence.

Example 6

Peptide-based mobility standards can be made that are resistant to proteolytic cleavage. A peptide pI standard was synthesized according to the method in Example 2, except that all E and K residues, which have an L-configuration, are replaced with residues of the corresponding D-configuration (i.e. D-Lys (k) and D-Glu (e) (AnaSpec, Inc. San Jose). The resulting purified peptide has the sequence $H_2N$—K(ATFB)

GkekekekGK(5-TAMRA)G-OH. This peptide is expected to have a higher resistance to proteases than does a corresponding peptide in which all residues have an L-configuration.

Example 7

Figure 3:
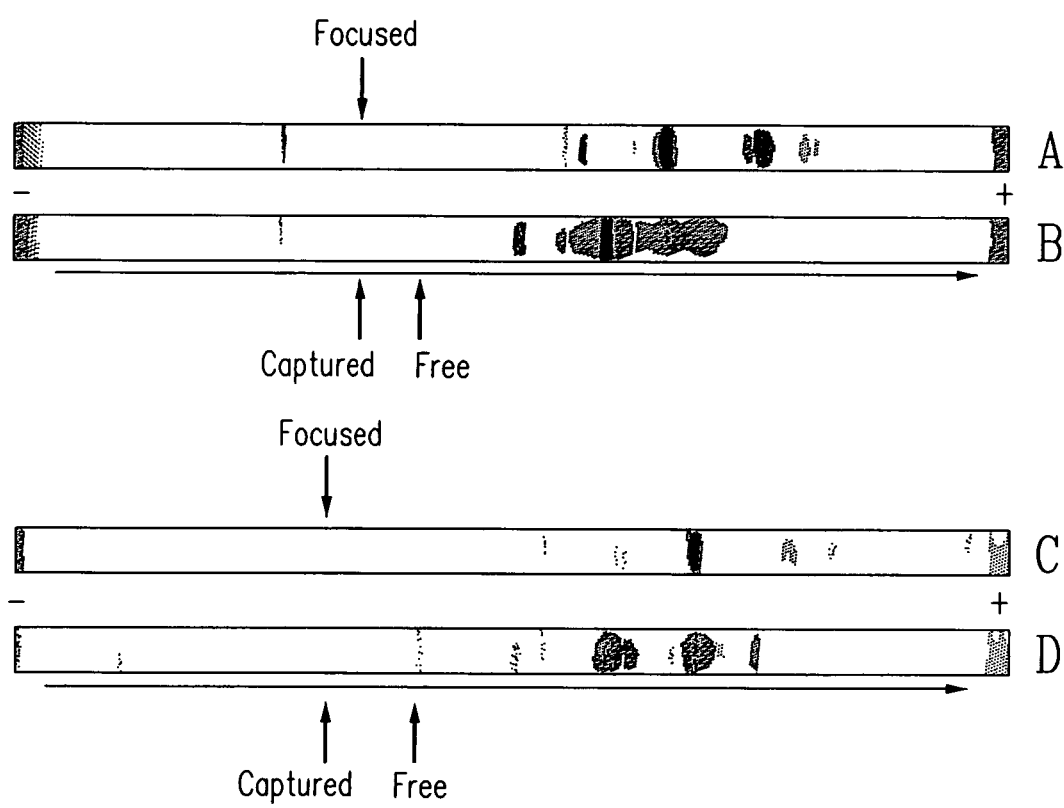
FIG. 3 illustrates capillaries showing immobilization efficiency of electrophoresis standards according to embodiments of the present teaching.

FIG. 3 shows the capture efficiency of isoelectric focusing standards without a reactive moiety (A and B) and a isoelectric focusing standards with a reactive moiety (C and D) in a capillary. Dye-labeled isoelectric focusing standards were loaded into a capillary, focused, and then immobilized in an ATFB-polyPEG matrix in the capillary by exposure to UV. Fluorescent images of the standard without a reactive moiety (A) and with a reactive moiety (C) show a clearly focused band within the capillary. The amount immobilized within the capillary was measured by replacing the isoelectric focusing buffers in the end chambers with 20 mM Tris Ci and electrophoresing the uncaptured bands away from the immobilized. The direction of electrophoresis is indicated by the arrow. After 400 sec electrophoresis was terminated and a fluorescence image was taken. Non-immobilized protein migrated away from the captured protein. Nearly the all of the isoelectric focusing standards without a reactive moiety (B) was free to be electrophoresed through the gel, away from the isoelectric focusing point. Far more of the isoelectric focusing standards with a reactive moiety was immobilized in the capillary (D).

Figure 4:
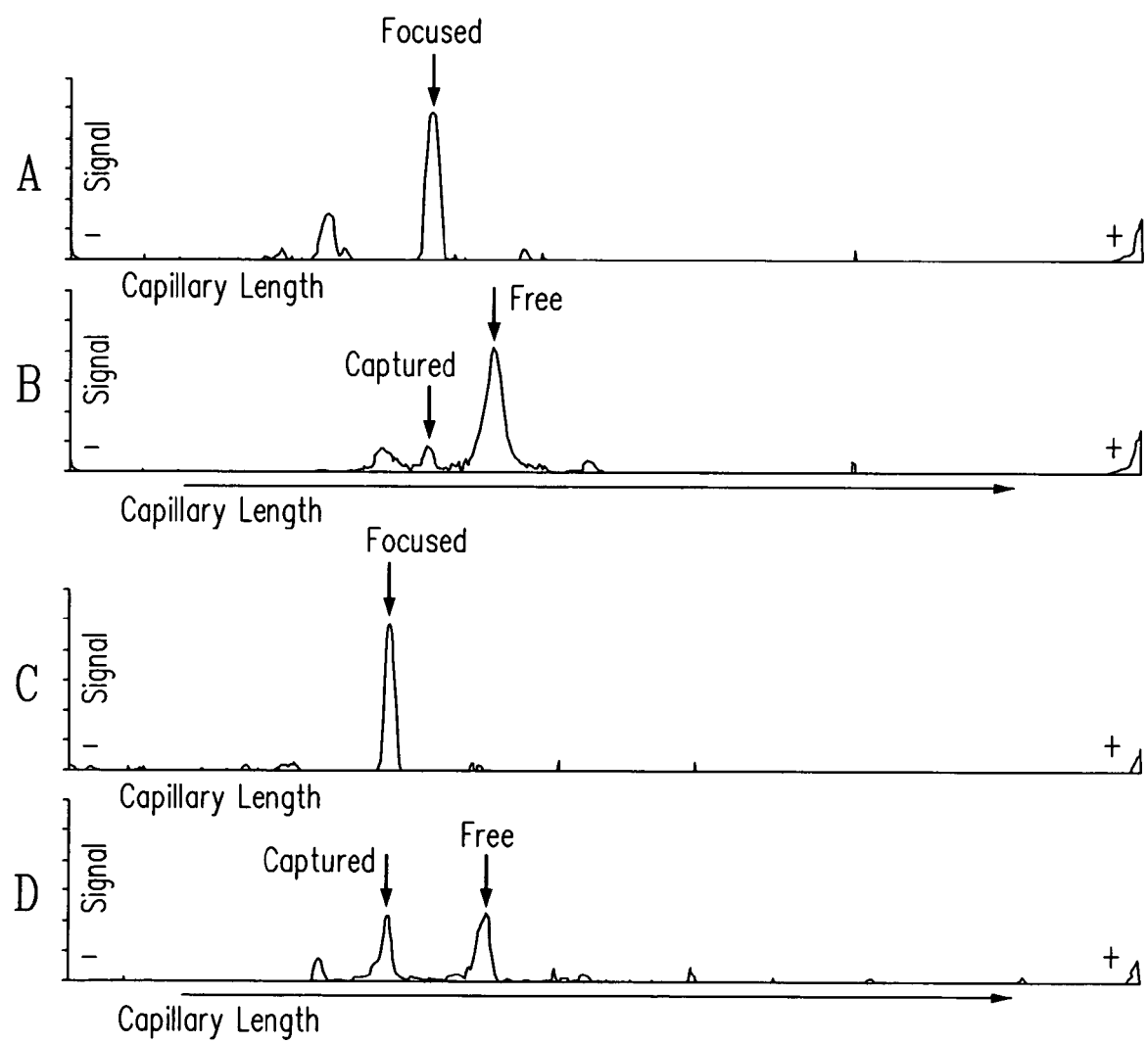
FIG. 4 illustrates densitometry data presented from the capillaries shown in FIG. 3.

FIG. 4 represents densitometry data from the capillaries shown in FIG. 3. Measurements taken from the CCD detector were used to plot the signal measured along the length of the capillary. Again, the standard without a reactive moiety (A) standards were focused and imaged. The buffers were exchanged and the uncaptured standard was electrophoresed away from the immobilized. Measurements of the peak area showed that about 5% of the standard without a reactive moiety was immobilized (B). When the same experiment was performed on the standard with a reactive moiety (C and D), about 40% of the standard was immobilized. The peaks of the immobilized and non-immobilized standards were compared. Immobilization was about 10 times better with the standard without a reactive moiety (D) then the standard lacking the standard without a reactive moiety (B).

Figure 5:
FIG. 5 illustrates chemiluminescent (A) and a fluorescent image (B) of electrophoresis standards in capillaries according to embodiments of the present teaching.

FIG. 5 shows the chemiluminescent (A) and a fluorescent image (B) of the same capillary showing the use of the invention. The proteins in a cell lysate were separated by their pI. A western blot like protocol was performed on the proteins immobilized within a capillary. The target protein visualized chemiluminescently (A) is AKT within a cell lysate. The fluorescent image (B) is of standards of the invention run in the same capillary. The approximate pI of the standards is shown.

Figure 6:
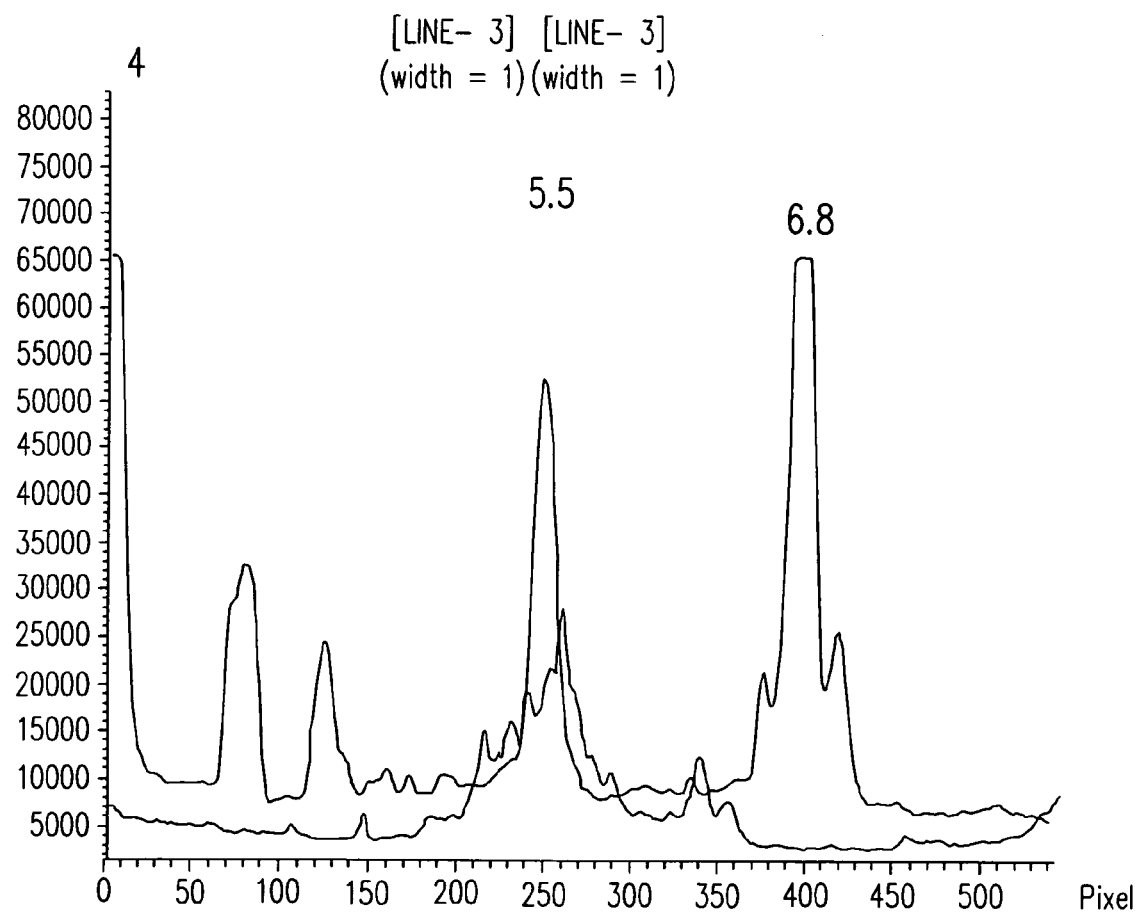
FIG. 6 is a histogram of chemiluminescent data (grey) superimposed over a histogram of fluorescent data (black) from a capillary shown in FIG. 5 illustrating how the mobility electrophoresis standards can be compared the mobility of an analyte.

FIG. 6 is a histogram of the chemiluminescent data (blue) superimposed over a histogram of the fluorescent data (black) from the capillary shown in FIG. 5 illustrating how the standards can be used to compare the mobility of standards against an analyte Example 8

The following are a list of peptide standards useful as electrophoresis standards in accordance with the present invention. This list is provided for illustration proposes only and in not intended to limit the invention in any way.

H₂N—K(ATFB)GAEHHK(5-TAMRA)G-OH
H₂N—K(ATFB)GAHEHEHEHEK(5-TAMRA)G-OH
H₂N—K(ATFB)GachhK(5-TAMRA)G-OH
H₂N—K(ATFB)GaheheheheK(5-TAMRA)G-OH
H₂N—K(ATFB)GaeeK(5-TAMRA)G-OH
H₂N—K(ATFB)GaeehK(5-TAMRA)G-OH
H₂N—K(ATFB)GaehehehekeK(5-TAMRA)G-OH
H₂N—K(ATFB)GaddrK(5-TAMRA)G-OH
H₂N—K(ATFB)GahehehehK(5-TAMRA)G-OH
H₂N—K(ATFB)GaehrK(5-TAMRA)G-OH
H₂N—K(ATFB)GaehhhrK(5-TAMRA)G-OH
H₂N—K(ATFB)GAKKKYYEEYRYYK(5-TAMRA)G-OH
H₂NK(ATFB)GAKKKYYEEYYYK(5-TAMRA)G-OH
H₂N—K(ATFB)GAEHHK(Biotin)G-OH
H₂N—K(ATFB)GAHEHEHEHEK(Biotin)G-OH
H₂N—K(BP)GAHEHEHEHEK(5-TAMRA)G-OH Lower case letters indicate D amino acids. In this example biotin labeled standards are detected using dye-labeled strepaviden.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

All patents, patent applications, publications, and references cited herein are expressly incorporated by reference to the same extent as if each individual publication or patent application was specifically and individually indicated to be incorporated by reference.

What is claimed is:

1. A method of determining the isoelectric point of one or more analytes by isoelectric focusing comprising the steps of:
    forming a pH gradient in a fluid path including one or more analytes and one or more standards, the one or more standards including one or more moieties, at least one of the one or more moieties being a at least one reactive moiety, when the at least one reactive moiety is activated to form an activated moiety, the activated moiety attaches the one or more standards to a substrate;
    focusing the one or more analytes at a position equal to the isoelectric point of each analyte from the one or more analytes and focusing the one or more standards at a position equal to the isoelectric point of each standard from the one or more standards;
    immobilizing the one or more analytes and the one or more standards in said fluid path by activating the at least one reactive moiety, the immobilizing being non-specific to any analyte from the one or more analytes;
    detecting one or more signals generated from the one or more analytes and the one or more standards; and
    determining the isoelectric point of each analyte from the one or more analytes by comparing the signals of the one or more analytes to the signals of the one or more standards.

2. The method of claim 1, wherein said fluid path is comprised of one or more capillaries.

3. The method of claim 1, wherein said fluid path is comprised of one or more channels in a microfluidic device.

4. The method of claim 1, wherein said fluid path is comprised of one or more gels.

5. A method of determining the isoelectric point of one or more analytes by isoelectric focusing comprising the steps of:
    generating an electric field to form a pH gradient in a fluid path including one or more analytes and one or more standards, the one or more standards including one or more reactive moieties configured to attach the one or more standards to a substrate;

immobilizing the one or more analytes and the one or more standards in said fluid path by activating the one or more reactive moieties, the immobilizing being non-specific to any analyte from the one or more analytes;

detecting one or more signals generated from the one or more analytes and the one or more standards when the one or more analytes and the one or more standards are at their respective isoelectric point; and generating data associated with a determination of the isoelectric point of each analyte from the one or more analytes by comparing the signals of the one or more analytes to the signals of the one or more standards.

6. The method of claim 5, wherein the one or more reactive moieties are activated to form at least one activated moiety, the activated moiety configured to attach the one or more standards to the substrate.

7. The method of claim 5, further comprising:

before the detecting, focusing the one or more analytes at a position equal to the isoelectric point of each analyte from the one or more analytes and focusing the one or more standards at a position equal to the isoelectric point of each standard from the one or more standards.

8. The method of claim 5, wherein the fluid path includes one of one or more capillaries, a microfluidic device or one or more gels.

* * * * *